United States Patent
Fujiyo et al.

(10) Patent No.: US 9,726,606 B2
(45) Date of Patent: Aug. 8, 2017

(54) DETECTION DEVICE

(71) Applicant: Konica Minolta, Inc., Tokyo (JP)

(72) Inventors: Ichiro Fujiyo, Osaka (JP); Tetsuya Noda, Tokyo (JP)

(73) Assignee: Konica Minolta, Inc., Tokyo (JP)

( * ) Notice: Subject to any disclaimer, the term of this patent is extended or adjusted under 35 U.S.C. 154(b) by 0 days.

(21) Appl. No.: 15/320,099

(22) PCT Filed: Jun. 16, 2015

(86) PCT No.: PCT/JP2015/067222
§ 371 (c)(1),
(2) Date: Dec. 19, 2016

(87) PCT Pub. No.: WO2015/194518
PCT Pub. Date: Dec. 23, 2015

(65) Prior Publication Data
US 2017/0138859 A1    May 18, 2017

(30) Foreign Application Priority Data
Jun. 19, 2014 (JP) .................................. 2014-126282

(51) Int. Cl.
*G01N 21/64* (2006.01)

(52) U.S. Cl.
CPC ....... *G01N 21/6428* (2013.01); *G01N 21/645* (2013.01); *G01N 2021/6439* (2013.01); *G01N 2021/6471* (2013.01)

(58) Field of Classification Search
CPC ............. G01N 21/345; G01N 21/6428; G01N 2021/6439; G01N 2021/3471
See application file for complete search history.

(56) References Cited

FOREIGN PATENT DOCUMENTS

JP          2014032148 A  *  2/2014
WO       2010/101052 A1     9/2010

OTHER PUBLICATIONS

Written Opinion of the International Searching Authority, from PCT/JP2015/067222 with an international filing date of Jun. 16, 2015, mailed on Sep. 8, 2015, 3 pgs., mailed from the Japanese Patent Office, Japan.

* cited by examiner

*Primary Examiner* — David Porta
*Assistant Examiner* — Faye Boosalis
(74) *Attorney, Agent, or Firm* — Baker & Hostetler LLP

(57) ABSTRACT

A detection device comprises a chip holder, a light source, a light-guide rod, a wavelength separation filter, and an optical sensor. Given the relationship between the angle of incidence and light intensity of fluorescence on a light reception surface of the optical sensor, the optical transmittance of the wavelength separation filter at the dominant wavelength of the rays of fluorescence incident on the light reception surface at a peak angle of incidence at which the light intensity is the highest is greater than the optical transmittance of the wavelength separation filter at the dominant wavelength of the rays of excitation light incident on the light reception surface at the peak angle of incidence and is higher than the optical transmittance of the wavelength separation filter at the dominant wavelength of the rays of fluorescence incident on the light reception surface at an angle of incidence of 0 DEG.

10 Claims, 8 Drawing Sheets

DETECTION DEVICE

CROSS-REFERENCE TO RELATED APPLICATIONS

This application is a U.S. National Stage filing, under 35 U.S.C. 371, of International Application No. PCT/JP2015/067222, filed Jun. 16, 2015, which claims the benefit of Japanese application number 2014-126282, filed Jun. 19, 2014, the disclosures of which, including the specification, drawings, and abstract, are incorporated herein by reference in their entirety.

BACKGROUND OF THE INVENTION

Technical Field

The present invention relates to a detection device that detects fluorescence emitted from a label material labelling a detection object substance to detect the detection object substance.

Background Art

Highly sensitive and quantitative detection of a minute amount of a detection object substance such as protein and DNA in laboratory tests makes it possible to perform treatment by quickly determining the patient's condition. There is therefore a need for a detection device for quantitatively measuring a minute amount of detection object substance with high sensitivity.

A detection device utilizing surface plasmon-field enhanced fluorescence spectroscopy (hereinafter abbreviated as "SPFS") is known as a detection device which can detect a detection object substance with high sensitivity (see, for example, PTL 1).

In the detection device disclosed in PTL 1, a sensor chip including a prism formed of a dielectric, a metal film formed on the prism, a capturing body (for example antibody) fixed on the metal film is used. When a sample containing a detection object substance is supplied on the metal film, the detection object substance is captured by the capturing body (primary reaction). The detection object substance thus captured is further labeled by a fluorescence material (secondary reaction). In this state, when the metal film is irradiated with excitation light through the prism at an angle at which surface plasmon resonance is caused, localized-field light can be generated on the surface of the metal film. With this localized-field light, the fluorescence material for labelling the captured detection object substance on the metal film is selectively excited, and fluorescence emitted from the fluorescence material is observed. In the detection device, the fluorescence is detected to detect the presence or the amount of the detection object substance.

The above-mentioned detection device uses highly sensitive light sensors such as a photomultiplier tube (PMT) and an avalanche photodiode (APD) to quantitatively detect weak fluorescence. In addition, a wavelength separation filter (wavelength selecting member) such as an interference filter and a color filter is used to detect weak fluorescence with a high S/N ratio. Further, a light guiding member having a columnar shape that condenses weak fluorescence is disposed at a position before the light sensor on the light path of the fluorescence. The fluorescence emitted from the fluorescence material is incident on one end surface (incidence surface) of the light guiding member, and is guided by being repeatedly reflected on the inside, and then emitted from the other end surface (emission surface). The wavelength separation filter included in the detection device removes various light rays other than fluorescence. Accordingly, only the fluorescence of the detection object reaches the light reception surface of the light sensor.

CITATION LIST

Patent Literature

PTL 1
WO2010/101052

SUMMARY OF THE INVENTION

Technical Problem

However, in the detection device disclosed in PTL 1, the relationship between the incident angle and the light quantity of the fluorescence at the light reception surface of the light sensor and the wavelength separation filter is not considered. Consequently, in the case where a wavelength separation filter whose wavelength separation property has angle dependence is used, the most of the fluorescence may be removed or various light rays other than the fluorescence may not be sufficiently removed unless the wavelength separation filter which can appropriately perform wavelength separation for a light beam whose incident angle is an incident angle at which the light quantity is maximized is used. In this case, disadvantageously, the intensity of the various light rays is increased while the intensity of the fluorescence is reduced, and consequently the S/N ratio is reduced. In view of the foregoing, the detection device disclosed in PTL 1 has a room for improvement in S/N ratio. As described above, in order to produce a chalcogenide glass optical element, various requirements need to be satisfied, a production process becomes special, and therefore a simpler production method has been demanded. A raw material for forming chalcogenide glass is expensive, and it is also required to reduce a material discarded in a production process.

An object of the present invention is to provide a detection device including a light guiding member (light guiding rod) which can efficiently detect fluorescence with a high S/N ratio, while preventing upsizing.

Solution to Problem

To solve the above-mentioned problems, a detection device according to an embodiment of the present invention is configured to detect a detection object substance by detecting fluorescence emitted from a fluorescence material labeling the detection object substance, the detection device including: a chip holder configured to hold a detection chip including a detection object region in which a capturing body for capturing the detection object substance is fixed; a light source for irradiating the detection chip held by the chip holder with excitation light; a light guiding rod configured to allow incidence of fluorescence emitted from a fluorescence material labeling the detection object substance captured by the capturing body at an incidence surface located at one end of the light guiding rod, and emit the fluorescence from an emission surface located at another end of the light guiding rod; a light sensor having a light reception surface perpendicular to an axis direction of the light guiding rod, the light sensor being configured to detect the fluorescence; and a wavelength separation filter disposed along a direction perpendicular to the axis direction of the light guiding rod at a position between the detection chip and the light guiding rod, or between the light guiding rod and the light sensor, the wavelength separation filter being configured to separate the fluorescence and unnecessary light other than the fluorescence from each other. In a relationship between a light quantity and an incident angle of the fluorescence at the light reception surface, a peak incident angle which is an incident angle at which the light quantity is maximized is an angle other than 0 degrees, and a light transmittance of the wavelength separation filter for a light beam of a main wavelength of the fluorescence which is incident on the light reception surface at the peak incident angle is greater than a light transmittance of the wavelength separation filter for a light beam of a main wavelength of the excitation light which is incident on the light reception surface at the peak incident angle, and greater than a light transmittance of the wavelength separation filter for a light beam of a main wavelength of the fluorescence which is incident on the light reception surface at an incident angle of 0 degrees.

Advantageous Effects of Invention

According to the present invention, it is possible to provide a detection device which can efficiently detect fluorescence with a high S/N ratio, while preventing upsizing.

DESCRIPTION OF EMBODIMENTS

In the following, an embodiment of the present invention is described in detail with reference to the accompanying drawings. In the following description, as a typical example of a detection device according to the embodiment of the present invention, a surface plasmon enhanced fluorescence measurement device (hereinafter also referred to as "SPFS device") that detects a detection object substance by utilizing surface plasmon resonance (SPR) is described.

(Configuration of SPFS Device)

An SPFS device is used in a state where a detection chip having a prism formed of a dielectric and a metal film formed on one surface of the prism is attached to the device. A capturing body for capturing the detection object substance is fixed on the metal film. When a sample containing a detection object substance is provided on the metal film, the detection object substance is captured by the capturing body. At this time, the detection object substance may or may not be labeled by a fluorescence material. When the captured detection object substance has not been labeled by the fluorescence material, the captured detection object substance is further labeled by the fluorescence material. In this state, excitation light is applied to a prism provided with the metal film on the surface thereof in such a manner as to satisfy the total reflection condition. As a result, interaction (surface plasmon resonance) between the excitation light and the free electrons in the metal film occurs, and localized light is generated. Generally, this localized light is called also as "enhanced electric field" or "enhanced evanescent light," and with the localized light, variation of the physical quantity in a region around the surface of the metal film can be measured. With this localized-field light, the fluorescence material for labelling the captured detection object substance on the metal film is selectively excited, and fluorescence emitted from the fluorescence material is observed. The SPFS device measures the light quantity of the fluorescence to detect the presence or the amount of the detection object substance.

Figure 1:
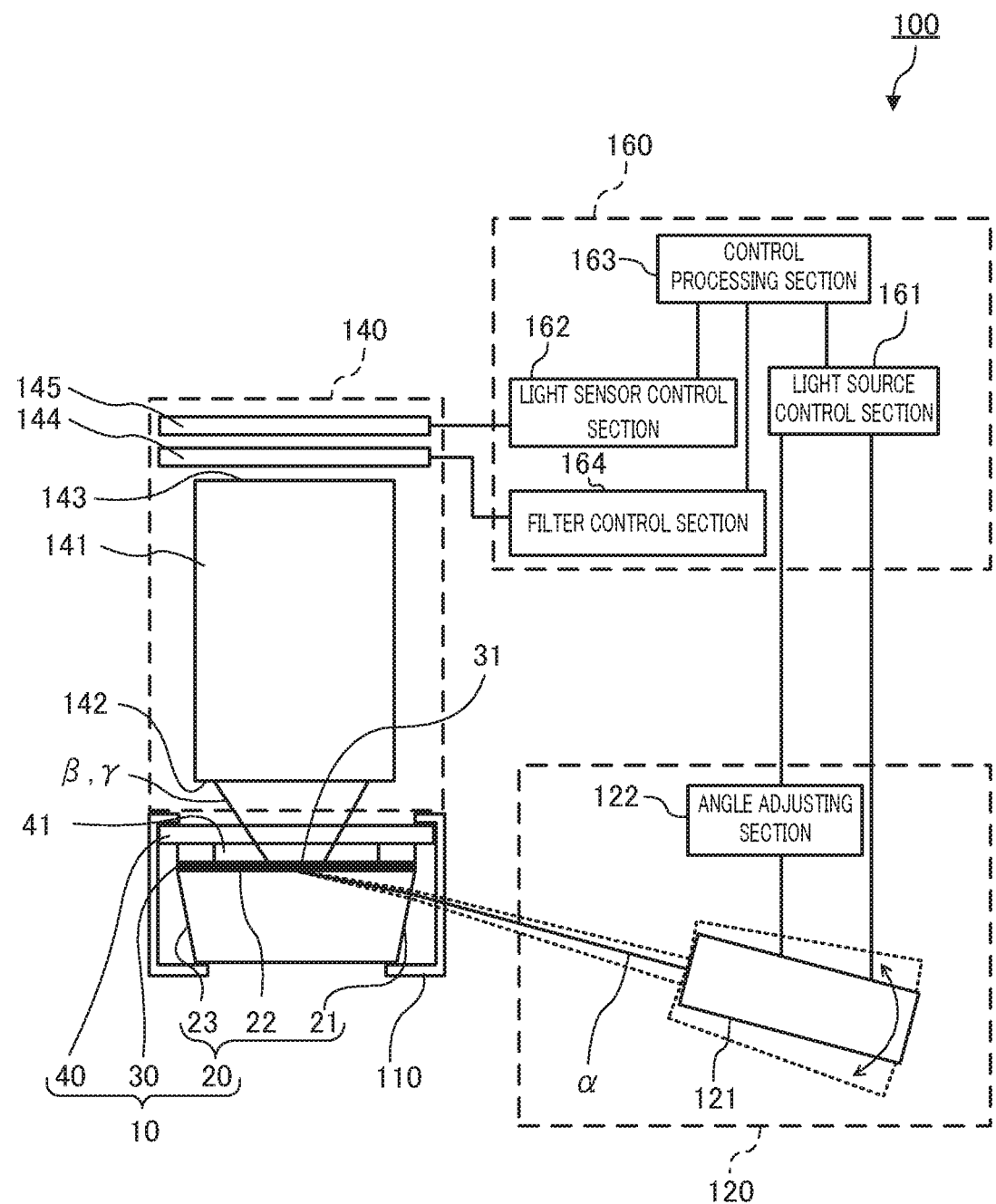
FIG. 1 illustrates a configuration of a surface plasmon enhanced fluorescence measurement device according to an embodiment of the present invention.

FIG. 1 illustrates a configuration of SPFS device 100 according to the embodiment 1 of the present invention. As illustrated in FIG. 1, SPFS device 100 includes chip holder 110 for detachably holding detection chip 10, excitation optical system unit 120 for irradiating detection chip 10 with excitation light α, light reception optical system 140 for detecting light emitted from detection chip 10 (plasmon scattering light β or fluorescence γ), and control section 160 for controlling the above-mentioned components. SPFS device 100 is used in a state where detection chip 10 is attached in chip holder 110. For such a configuration, detection chip 10 is described first, and then the components of SPFS device 100 are described.

As illustrated in FIG. 1, detection chip 10 includes prism 20 having incidence surface 21, film formation surface 22 and emission surface 23, metal film 30 formed on film formation surface 22, and channel closure 40 disposed on film formation surface 22 or metal film 30. Normally, detection chip 10 is replaced for each detection (analysis).

Prism 20 is a dielectric which is transparent to excitation light α. Prism 20 includes incidence surface 21, film formation surface 22 and emission surface 23. Incidence surface 21 is a surface through which excitation light α from excitation optical system unit 120 enters prism 20. Metal film 30 is formed on film formation surface 22. Excitation light α having entered prism 20 is reflected by metal film 30. To be more specific, the excitation light α having entered prism 20 is reflected by the interface (film formation surface 22) between prism 20 and metal film 30. Emission surface 23 is a surface through which excitation light α reflected by metal film 30 is emitted out of prism 20. The shape of prism 20 is not limited. In the present embodiment, the shape of prism 20 is a column whose bottom surface is a trapezoid.

The surface corresponding to a bottom side of the trapezoid is film formation surface 22. The surface corresponding to one of the legs is incidence surface 21, and the surface corresponding to the other of the legs is emission surface 23. Preferably, the trapezoid serving as the bottom surface is an isosceles trapezoid. With such a configuration, incidence surface 21 and emission surface 23 are symmetrical, and the S wave component of excitation light α does not easily remain in prism 20. Incidence surface 21 is formed such that excitation light α does not return to excitation optical system unit 120. The reason for this is that, if excitation light α returns to the laser diode serving as the excitation light source, the excitation state of the laser diode is disturbed, and the wavelength and the output of the excitation light α is varied. In view of this, the angle of incidence surface 21 is set within a scanning range around the ideal enhanced angle such that the excitation light α is not perpendicularly incident on incidence surface 21. For example, the angle between incidence surface 21 and film formation surface 22, and the angle between film formation surface 22 and emission surface 23 are each approximately 80 degrees. Examples of the material of prism 20 include a resin and glass. Preferably, the material of prism 20 is a resin which has a refractive index of 1.4 to 1.6 and causes a small birefringence.

Metal film 30 is formed on film formation surface 22 of prism 20. When metal film 30 is provided, interaction (surface plasmon resonance; SPR) occurs between the photon of excitation light α which is incident on film formation surface 22 under the total reflection condition and the free electron in metal film 30, and thus localized-field light can be generated on the surface of metal film 30. The material of metal film 30 is not limited as long as surface plasmon resonance can be caused. Examples of the material of metal film 30 include gold, silver, copper, aluminum, and their alloys. In the present embodiment, metal film 30 is a thin film formed of gold. The formation method for metal film 30 is not limited. Examples of the formation method for metal film 30 include sputtering, deposition, and plating. Preferably, the thickness of metal film 30 is, but not limited to, 30 to 70 nm.

In addition, although not illustrated in the drawings, a capturing body for capturing the detection object substance is fixed on a surface of prism 20 which faces away from metal film 30. By fixing the capturing body, the detection object substance can be selectively detected. Thus at least a part of the surface of metal film 30 is set as detection object region 31. In the present embodiment, a center portion of the surface of metal film 30 is set as detection object region 31. The capturing body is uniformly fixed in detection object region 31. The "detection object region" is a region where the capturing body for capturing the detection object substance is fixed. The type of the capturing body is not limited as long as the detection object substance can be captured. For example, the capturing body is an antibody or its fragments which can be specifically coupled with the detection object substance.

Channel closure 40 is disposed on a surface of metal film 30 which faces away from prism 20 with channel 41 interposed therebetween. Channel closure 40 may be disposed on film formation surface 22 with channel 41 interposed therebetween. Together with metal film 30 (and prism 20), channel closure 40 forms flow channel 41 through which liquid such as a sample, fluorescence labeling solution, and washing solution flows. Detection object region 31 is exposed to the inside of channel 41. Both ends of channel 41 are respectively connected to the inlet and outlet (both omitted in the drawing) formed on the top surface of channel closure 40. When liquid is injected into channel 41, the liquid makes contact with the capturing body in detection object region 31 in channel 41. Channel closure 40 is formed of a material transparent to light (plasmon scattering light β and fluorescence γ) emitted from detection object region 31 of metal film 30. Examples of the material of channel closure 40 include a resin. As long as the above-mentioned light can be guided to light reception optical system 140, a part of channel closure 40 may be formed of an opaque material. Channel closure 40 is joined to metal film 30 or prism 20 by bonding using a double-sided tape or an adhesive agent, laser welding, ultrasound welding, or pressure fixing using a clamping member, for example.

As illustrated in FIG. 1, excitation light α guided to prism 20 enters prism 20 at incidence surface 21. The excitation light α having entered prism 20 is incident on the interface (film formation surface 22) between prism 20 and metal film 30 at a total reflection angle (at an angle at which surface plasmon resonance occurs). The reflection light from the interface is emitted out of prism 20 from emission surface 23 (not shown in the drawing). Meanwhile, when excitation light α is incident on the interface at an angle at which surface plasmon resonance occurs, plasmon scattering light β, fluorescence γ and the like are emitted from detection object region 31 in the direction toward light reception optical system 140.

Next, the components of SPFS device 100 are described. As described above, SPFS device 100 includes chip holder 110, excitation optical system unit 120, light reception optical system 140 and control section 160.

Chip holder 110 holds detection chip 10 at a predetermined position. Detection chip 10 is irradiated with excitation light α from excitation optical system unit 120 in the state where detection chip 10 is held by chip holder 110. At this time, plasmon scattering light β having a wavelength identical to that of excitation light α, fluorescence γ emitted from the fluorescence material and the like are emitted upward from detection object region 31. In addition, excitation light α is reflected by the interface between prism 20 and metal film 30, and emitted to the outside of prism 20 (not shown in the drawing).

Excitation optical system unit 120 includes light source unit 121 that emits excitation light α, and angle adjusting section 122 that adjusts the incident angle of excitation light α with respect to the interface (film formation surface 22) between prism 20 and metal film 30.

Light source unit 121 includes a laser diode (hereinafter also referred to as "LD") as an excitation light source, and emits excitation light α (single mode laser light) toward incidence surface 21 of prism 20 of detection chip 10 held by chip holder 110. To be more specific, light source unit 121 emits excitation light α at a total reflection angle to the rear surface of metal film 30 corresponding to the region in which the capturing body is fixed from prism 20 side of detection chip 10. For example, light source unit 121 includes an LD unit, a shaper and a shaping optical system (which are omitted in the drawing).

The LD unit emits collimated excitation light α having a constant wavelength and a constant light quantity such that the irradiation spot on the interface (film formation surface 22) between prism 20 and metal film 30 has a substantially circular shape. The LD unit includes an LD as an excitation light source, a collimator that collimates excitation light α emitted from the LD, and a temperature adjusting circuit that adjusts the light quantity of excitation light α to a constant value. The excitation light α emitted from the LD has a flat outline shape even after it is collimated. In view of this, the LD is held at a predetermined orientation, or a slit having a predetermined shape is inserted to a shaping optical system described later such that the irradiation spot on the interface (film formation surface 22) has a substantially circular shape. In addition, the wavelength and the light quantity of excitation light α emitted from the LD vary depending on the temperature. In view of this, the temperature adjusting circuit monitors the light quantity of the light diverged from the collimated excitation light α with use of a photodiode and the like, and adjusts the temperature of the LD such that the wavelength and the light quantity of the excitation light α is adjusted to a constant value with use of a heater, a Peltier element and the like.

The shaper includes a band pass filter (hereinafter also referred to as "BPF") and a linear polarization filter (hereinafter also referred to as "LP"), and shapes the excitation light α emitted from the LD unit. Since the excitation light α from the LD unit has a slight wavelength distribution width, BPF changes the excitation light α from the LD unit to narrowband light composed only of a center wavelength. In addition, since the excitation light α from the LD unit is not complete linear polarization, the LP changes the excitation light α from the LD unit to complete linear polarization light. The shaper may include a half-wave plate that adjusts the polarization direction of excitation light α such that the P wave component is incident on metal film 30.

The shaping optical system adjusts the beam diameter, the outline shape and the like of excitation light α such that the irradiation spot on the interface (film formation surface 22) between prism 20 and metal film 30 has a circular shape of a predetermined size. The excitation light α emitted from the shaping optical system is applied to prism 20 of detection chip 10. The shaping optical system is a slit, a zooming section, or the like, for example. The size of the irradiation spot of excitation light α on one surface of metal film 30 (the surface facing away from prism 20) is adjusted to a size smaller than the size of detection object region 31 on the other surface of metal film 30 (the surface facing away from light guiding rod 141). With such a configuration, it is possible to prevent the irradiation spot from being displaced from detection object region 31 even when the position of the irradiation spot is slightly shifted due to errors of the parameters of prism 20.

It is to be noted that the type of the light source included in light source unit 121 is not limited, and may not be the LD. Examples of the light source include a light-emitting diode, a mercury lamp, and other laser light sources. In the case where the light emitted from the light source is not a beam, the light emitted from the light source is converted to a beam by a lens, a mirror, a slit or the like. In addition, in the case where the light emitted from the light source is not monochromatic light, the light emitted from the light source is converted to monochromatic light by a diffraction grid or the like. Further, in the case where the light emitted from the light source is not linear polarization, the light emitted from the light source is converted to light of linear polarization by a polarizer or the like.

Angle adjusting section 122 adjusts the incident angle of excitation light α to metal film 30 (the interface (film formation surface 22) between prism 20 and metal film 30). Angle adjusting section 122 relatively rotates the optical axis of excitation light α and chip holder 110 so as to apply excitation light α to a predetermined portion (rear side of detection object region 31) of metal film 30 (film formation surface 22) at a predetermined incident angle. In the present embodiment, angle adjusting section 122 rotates light source unit 121 about the axis orthogonal to the optical axis of excitation light α. At this time, the position of the rotation axis is set such that the irradiation position on metal film 30 (film formation surface 22) is not substantially moved when the incident angle is scanned. For example, when the position of the rotation center is set at a position near the intersection of the optical axes of two rays of excitation light α at both ends of the scanning range of the incident angle (at a position between the irradiation position on film formation surface 22 and incidence surface 21 of prism 20), the shift of the irradiation position can be minimized.

Light reception optical system 140 is disposed to face the surface (detection object region 31) of metal film 30 facing away from prism 20 in detection chip 10 held by chip holder 110. Light reception optical system 140 detects light emitted from metal film 30 (plasmon scattering light β and fluorescence γ). Light reception optical system 140 includes light guiding rod 141, wavelength separation filter 144 and light sensor 145.

Light guiding rod 141 includes incidence surface 142 and emission surface 143. Light guiding rod 141 has light transmissivity, and guides light (plasmon scattering light β or fluorescence γ) emitted from detection object region 31 (metal film 30 and the region around metal film 30) to light sensor 145. In SPFS device 100 according to the present embodiment, light guiding rod 141 is formed in a predetermined shape and size. Details of light guiding rod 141 will be described later.

Wavelength separation filter 144 allows light having a predetermined wavelength to pass therethrough, and blocks the light having wavelengths other than the predetermined wavelength (wavelength separation property). Wavelength separation filter 144 is a long pass filter or a band pass filter, for example. In the present embodiment, wavelength separation filter 144 is a long pass filter. Preferably, wavelength separation filter 144 blocks light (plasmon scattering light β) having the wavelength of excitation light α, while allowing only fluorescence γ to pass therethrough. As described later, the wavelength separation property of wavelength separation filter 144 has angle dependence.

Wavelength separation filter 144 is disposed along a direction perpendicular to the axis direction of light guiding rod 141 at a position between chip holder 110 (detection chip 10) and light guiding rod 141, or a position between light guiding rod 141 and light sensor 145. In the present embodiment, wavelength separation filter 144 is disposed at a position between light guiding rod 141 and light sensor 145. The "axis direction of light guiding rod 141" is a direction from the center of incidence surface 142 of light guiding rod 141 to the center of emission surface 143 of light guiding rod 141. Although not illustrated in the drawings, wavelength separation filter 144 is configured to be movable between a position on the light path of light reception optical system 140 and a position outside the light path of light reception optical system 140 under control of filter control section 164.

The type of wavelength separation filter 144 is not limited as long as fluorescence γ can pass therethrough, and unnecessary light other than fluorescence γ can be separated therefrom, and, the wavelength separation property of the filter has angle dependence. Examples of wavelength separation filter 144 in which the wavelength separation property of the filter has angle dependence include an interference filter including one or more dielectric multi-layer films. Details of wavelength separation filter 144 will be described later.

Light sensor 145 detects light (fluorescence γ or plasmon scattering light β) emitted from detection object region 31. Light sensor 145 includes light reception surface 146 that is perpendicular to the axis direction of light guiding rod 141. Light sensor 145 detects light which is guided by light guiding rod 141 and reaches light reception surface 146. The type of light sensor 145 is not limited as long as weak fluorescence γ can be detected. Examples of light sensor 145 include a photomultiplier tube and an avalanche photodiode (APD) having high sensitivity and S/N ratio, and the like, for example.

Control section 160 unitarily performs control of driving sections, quantification of the light reception amount of light sensor 145 and the like. In the present embodiment, control section 160 includes light source control section 161 that controls light source unit 121, light sensor control section 162 that controls light sensor 145, filter control section 164 that controls a filter movement section (omitted in the drawing), and control processing section 163. Control processing section 163 comprehensively controls light source control section 161, light sensor control section 162 and filter control section 164, so as to control the entire operation of SPFS device 100. Control section 160 is a computer configured to execute software, for example.

(Configuration of Light Guiding Rod)

Figure 2:
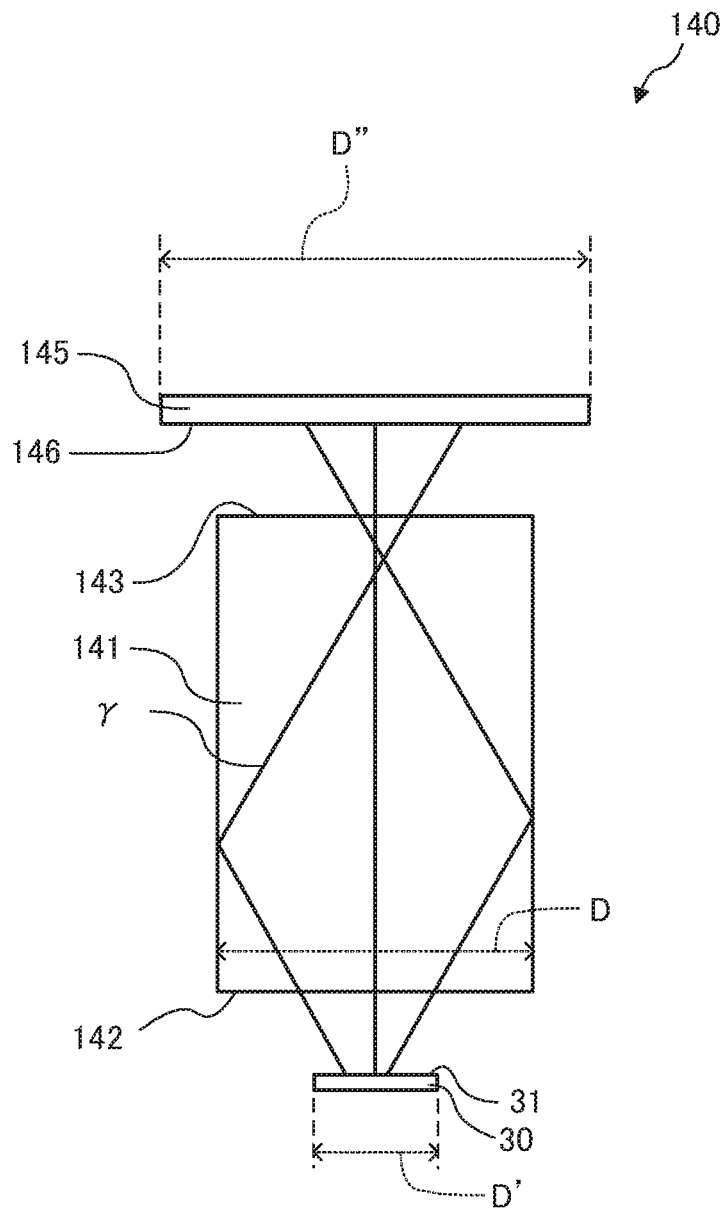
FIG. 2 illustrates a positional relationship between a detection object region, a light guiding rod and a light reception surface of a light sensor.

Next, light guiding rod 141 is described in detail. FIG. 2 illustrates a positional relationship of detection object region 31, light guiding rod 141 and light reception surface 146 of light sensor 145.

Light guiding rod 141 has light transmissivity. Light guiding rod 141 allows for incidence of light (plasmon scattering light β or fluorescence γ) emitted from detection object region 31 on incidence surface 142 located at one end thereof, and emits the light from emission surface 143 located at the other end thereof to guide the light to light sensor 145. The shape of light guiding rod 141 is not limited as long as light emitted from detection object region 31 can be guided to light sensor 145. In the present embodiment, light guiding rod 141 has a columnar shape whose cross-sectional area orthogonal to the axis direction of light guiding rod 141 from incidence surface 142 to emission surface 143 is constant. The material of light guiding rod 141 is not limited as long as plasmon scattering light β or fluorescence γ emitted from detection object region 31 can be guided to light sensor 145. Examples of the material of light guiding rod 141 include transparent resin and transparent glass. In addition, preferably, the refractive index of light guiding rod 141 is, but not limited to, about 1.4 to 2.0. In addition, a reflection film for preventing leakage of fluorescence γ incident on incidence surface 142 of light guiding rod 141 may be formed on a side surface of light guiding rod 141. The reflection film is a vapor deposition film of aluminum, gold or the like, for example.

As illustrated in FIG. 2, incidence surface 142 of light guiding rod 141 is one end surface (bottom surface) of a column, and is disposed to face the front surface of metal film 30 (detection object region 31). The distance between incidence surface 142 of light guiding rod 141 and detection object region 31 is about 0.5 to 5.0 mm. Diameter D of incidence surface 142 of light guiding rod 141 is greater than maximum length D' of detection object region 31. With this configuration, fluorescence γ emitted from detection object region 31 can efficiently enter light guiding rod 141. The "maximum length of the detection object region" is the maximum length of the line segments between two points on the external edge of detection object region 31. For example, when detection object region 31 has a circular shape, maximum length D' of detection object region 31 is the diameter thereof. When detection object region 31 has a rectangular shape, maximum length D' of detection object region 31 is the length of the diagonal thereof.

Emission surface 143 is the other end surface (bottom surface) of a column, and is disposed to face light reception surface 146 of light sensor 145 (or wavelength separation filter 144 disposed before sensor 145). The distance between emission surface 143 and light reception surface 146 of light sensor 145 is about 0.5 to 5.0 mm. Preferably, diameter D of emission surface 143 of light guiding rod 141 is smaller than maximum length D" of light reception surface 146 of light sensor 145. It is to be noted that the "maximum length of the light reception surface" is the maximum length of the line segments between two points on the external edge of light reception surface 146 of light sensor 145.

Figure 3A:
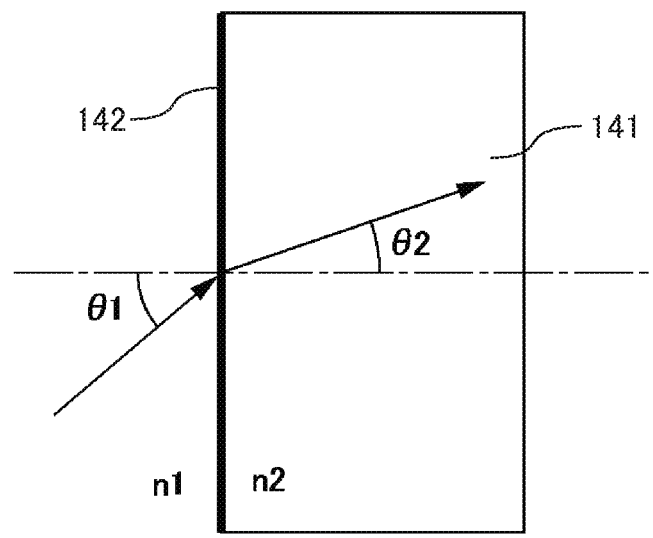
FIG. 3A is a schematic view illustrating an incident angle and a refraction angle of a light beam which is incident on the light guiding rod.
Figure 3B:
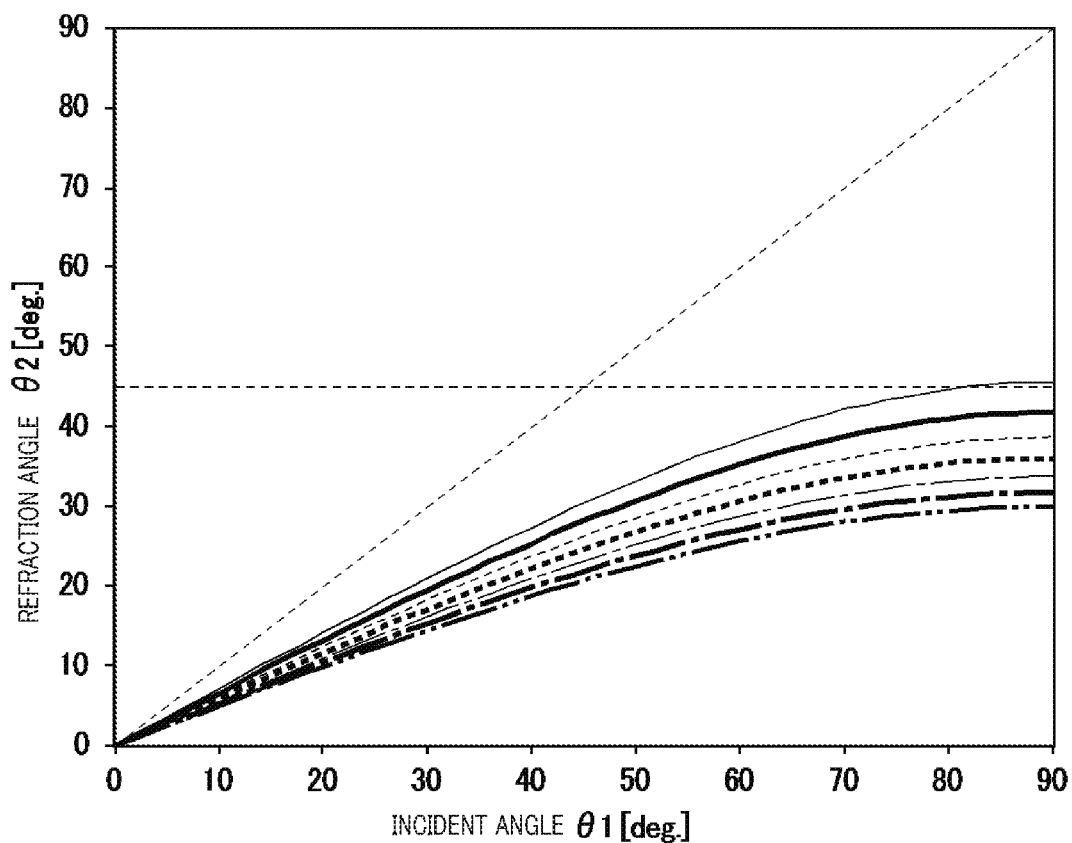
FIG. 3B is a graph showing a relationship between the incident angle and the refraction angle.

Next, the light path of light that advances in light guiding rod 141 is described. FIG. 3A is a schematic view illustrating incident angle θ1 and refraction angle θ2 of a light beam incident on light guiding rod 141. FIG. 3B is a graph showing a relationship between incident angle θ1 and refraction angle θ2.

As illustrated in FIG. 3A, it is known that n1×sin θ1=n2×sin θ2 holds (Snell's law) where θ1 represents the incident angle of light entering a medium (light guiding rod 141) having refractive index n2 from a medium (air layer) having refractive index n1, and θ2 represents the refraction angle of the light.

On the basis of Snell's law, refraction angles θ2 in light guiding rods 141 having respective refractive indices n2 of 1.4, 1.5, 1.6, 1.7, 1.8 and 2.0 were determined while changing incident angle θ1 from 0 to 90 degrees. FIG. 3B shows relationships between incident angle θ1 and refraction angle θ2 in the light guiding rods 141. In FIG. 3B, the uppermost curve (thin solid line) indicates a result obtained with light guiding rod 141 having refractive index n2 of 1.4. The second curve from the upper side (thick solid line) indicates a result obtained with light guiding rod 141 having refractive index n2 of 1.5. The third curve from the upper side (thin broken line) indicates a result obtained with light guiding rod 141 having refractive index n2 of 1.6. The fourth curve from the upper side (thick broken line) indicates a result obtained with light guiding rod 141 having refractive index n2 of 1.7. The fifth curve from the upper side (thin dashed line) indicates a result obtained with light guiding rod 141 having refractive index n2 of 1.8. The sixth curve from the upper side (thick dashed line) indicates a result obtained with light guiding rod 141 having refractive index n2 of 1.9. The lower most curve (thick chain double-dashed line) indicates a result obtained with light guiding rod 141 having refractive index n2 of 2.0.

As shown in FIG. 3B, it can be said that the greater the incident angle θ1, the smaller the change rate of refraction angle θ2. It can be said that, in light guiding rod 141 whose refractive index n2 is within the range of 1.4 to 2.0, the maximum angle of refraction angle θ2 is 45 degrees, and the light beam density increases within the range of 30 to 45 degrees of refraction angle θ2. In addition, it can be said that the greater the refractive index n2 of light guiding rod 141, the smaller the refraction angle θ2.

Figure 4A:
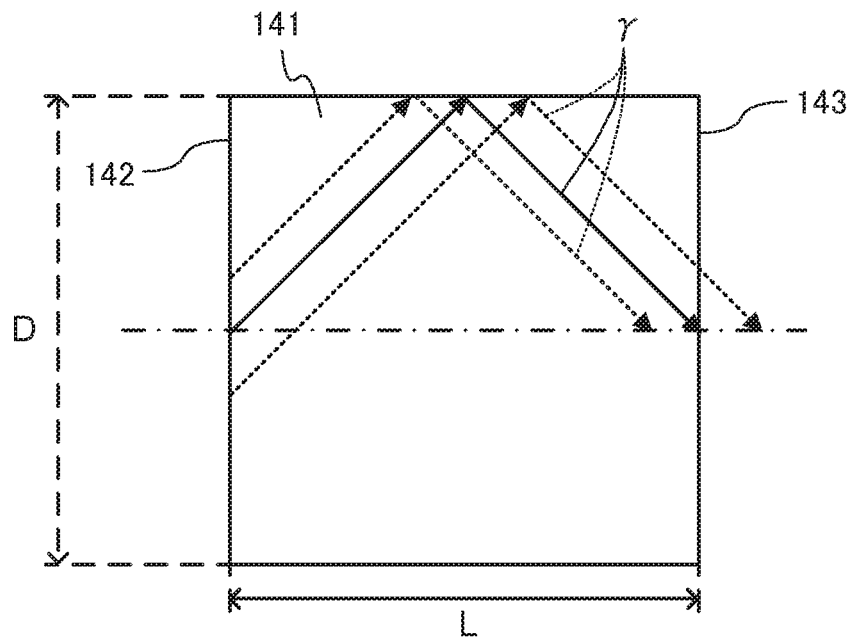
FIG. 4A illustrates a part of the light path of fluorescence advancing in the light guiding rod.
Figure 4B:
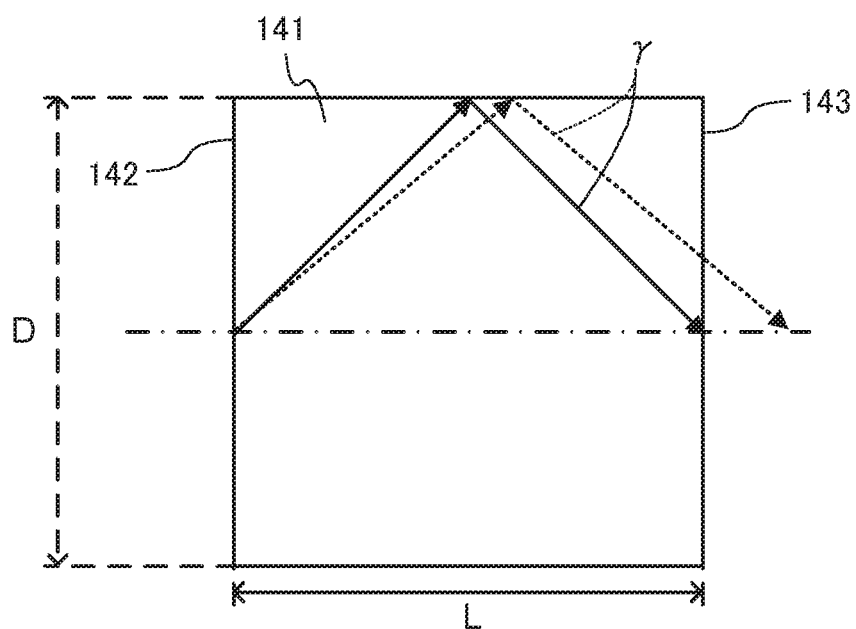
FIG. 4B illustrates a part of the light path of fluorescence advancing in the light guiding rod.

FIGS. 4A and 4B illustrate light paths of a part of fluorescence γ advancing in light guiding rod 141. FIG. 4A illustrates the difference in light path of fluorescence γ in light guiding rod 141 depending on the difference in incident position of fluorescence γ, and FIG. 4B illustrates the difference in light path of fluorescence γ in light guiding rod 141 depending on the difference in refractive index n2 of light guiding rod 141.

Here, the light path of fluorescence γ having a large light beam density and refraction angle θ2 of 45 degrees is examined. In FIG. 4A, the solid arrow indicates the light path of fluorescence γ incident on the center portion of incidence surface 142 of light guiding rod 141. The broken arrow indicates the light path of fluorescence γ incident on a portion other than the center portion of incidence surface 142 of light guiding rod 141. As the solid arrow indicates in FIG. 4A, it can be said that fluorescence γ which is incident on the center portion of incidence surface 142 of light guiding rod 141 and has refraction angle θ2 of 45 degrees passes through the center portion in the radial direction at a position remote from incidence surface 142 by D representing the diameter of incidence surface 142. In addition, as the broken arrow indicates in FIG. 4A, fluorescence γ which is incident on a portion shifted from the center portion of incidence surface 142 of light guiding rod 141, and has refraction angle θ2 of 45 degrees passes through the center portion in the radial direction at a position near the position remote from incidence surface 142 by D representing the diameter of incidence surface 142.

Next, the difference in light path of fluorescence γ incident on the center portion of incidence surface 142 of light guiding rod 141 depending on the difference in refractive index n2 of light guiding rod 141 is examined. In FIG. 4B, the solid arrow indicates the light path of fluorescence γ advancing in light guiding rod 141 having refractive index n2 of 1.4. The broken arrow indicates the light path of fluorescence γ advancing in light guiding rod 141 having refractive index n2 of 1.8.

As the solid arrow indicates in FIG. 4B, it can be said that fluorescence γ which is incident on the center portion of incidence surface 142 of light guiding rod 141 having refractive index n2 of 1.4, and has refraction angle θ2 of 45 degrees passes through the center portion in the radial direction at a position remote from incidence surface 142 by D representing the diameter of incidence surface 142. In addition, as the broken arrow indicates in FIG. 4B, it can be said that fluorescence γ which is incident on the center portion of incidence surface 142 of light guiding rod 141 having refractive index n2 of 1.8 passes through the center portion in the radial direction at a position remote from incidence surface 142 by a distance greater than D representing the diameter of incidence surface 142. In view of this, it can be said that, the greater the refractive index n2 of light guiding rod 141, the greater the distance from incidence surface 142 of light guiding rod 141 to the position where fluorescence γ passes through the center portion in the radial direction even when fluorescence γ has same refraction angle θ2.

Accordingly, in light guiding rod 141 of SPFS device 100 according to the present embodiment, axial length L is set based on refractive index n2 of light guiding rod 141 and diameter D of light guiding rod 141 so as to satisfy expression (1). With this configuration, fluorescence γ advancing in light guiding rod 141 can be condensed in a region around the center portion in the radial direction.

$$0.8n2D < L < 1.2n2D \quad (1)$$

Fluorescence γ emitted from emission surface 143 of light guiding rod 141 reaches light reception surface 146 of light sensor 145. Here, in the relationship between the incident angle and the light quantity of fluorescence γ at light reception surface 146, the incident angle at which the light quantity is maximized is referred to as peak incident angle. As described above, in light guiding rod 141, the light beam density increases within the range of 30 to 45 degrees of refraction angle θ2. Accordingly, the emission angle at which the light quantity is maximized at emission surface 143 of light guiding rod 141 is a predetermined angle other than 0 degrees (for example 35 degrees), and the peak incident angle at light reception surface 146 of light sensor 145 is also a predetermined angle other than 0 degrees (for example 35 degrees). In addition, as described above, wavelength separation filter 144 and light reception surface 146 of light sensor 145 are both perpendicular to the axis direction of light guiding rod 141. Accordingly, the incident angle of a light beam which is emitted from emission surface 143 of light guiding rod 141 and is incident on wavelength separation filter 144, and the incident angle of a light beam which passes through wavelength separation filter 144 and is incident on light reception surface 146 of light sensor 145 are equal to each other. That is, the peak incident angle at wavelength separation filter 144 is also a predetermined angle other than 0 degrees (for example 35 degrees).

(Wavelength Separation Property of Wavelength Separation Filter)

Figure 5A:
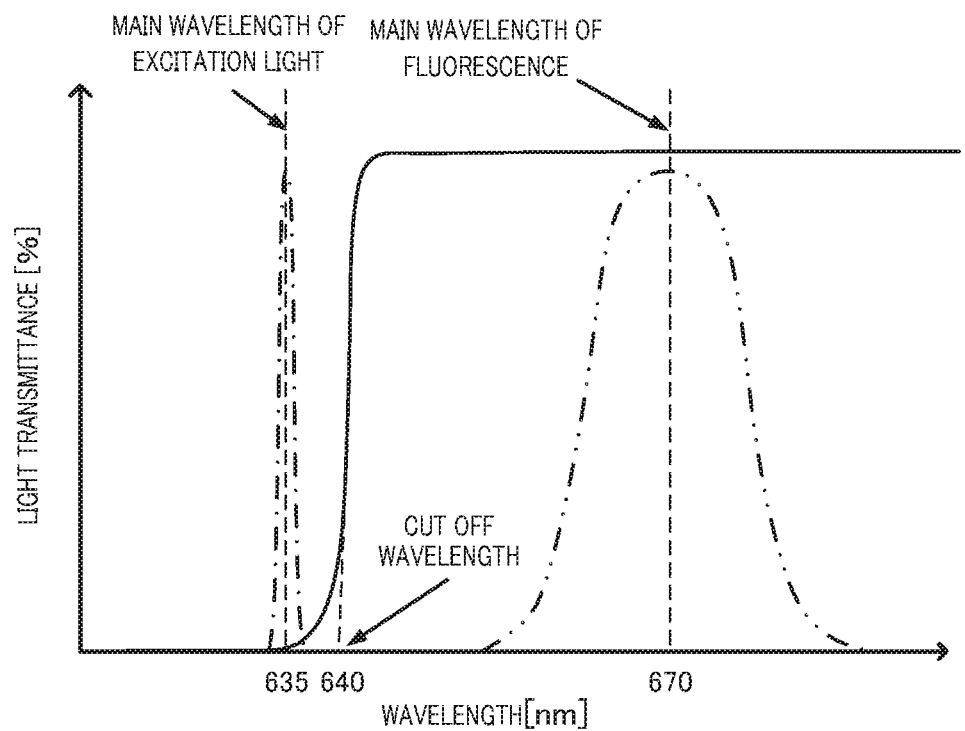
FIG. 5A is a graph showing a relationship between the wavelength and the light transmittance of the wavelength separation filter.
Figure 5B:
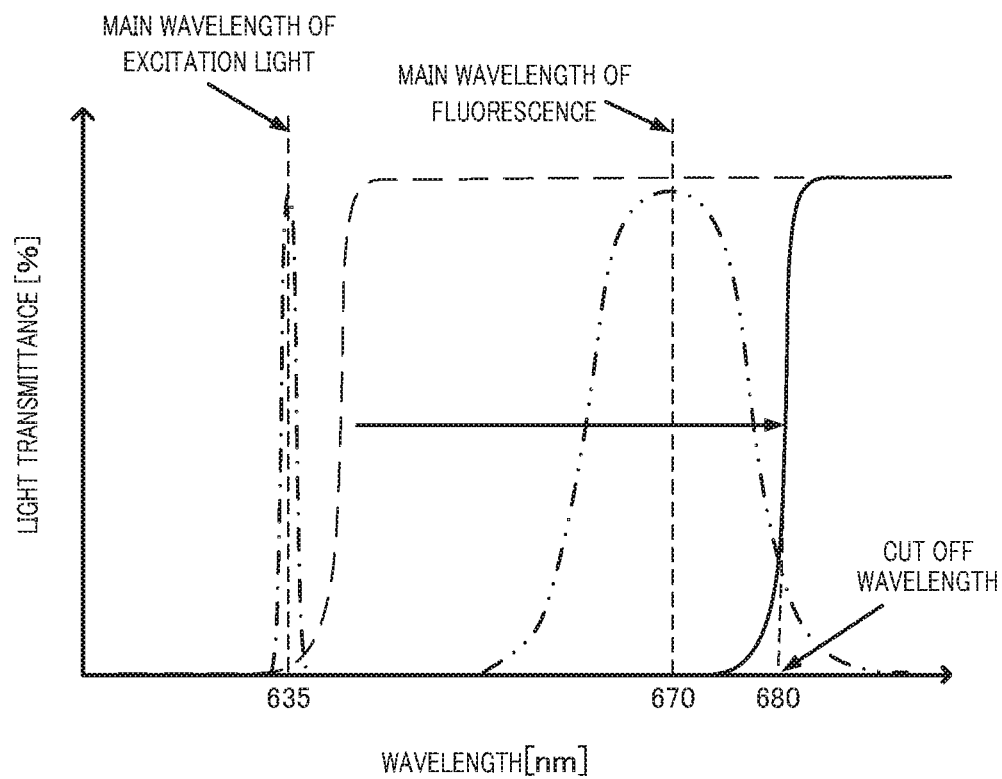
FIG. 5B is a graph showing a relationship between the wavelength and the light transmittance of the wavelength separation filter.

Next, the wavelength separation property of wavelength separation filter 144 used in the present embodiment is described. FIGS. 5A and 5B are drawings for describing the angle dependence of the wavelength separation property of wavelength separation filter 144 (long pass filter) used in the present embodiment. FIG. 5A shows the wavelength separation property of wavelength separation filter 144 for a light beam whose incident angle is a peak incident angle (for example 35 degrees), and FIG. 5B shows the wavelength separation property of wavelength separation filter 144 for a light beam whose incident angle is 0 degrees. In FIG. 5A and FIG. 5B, the solid line indicates the light transmittance of wavelength separation filter 144 whose cut off wavelength for a light beam whose incident angle is a peak incident angle (35 degrees) is 640 nm, and whose cut off wavelength for a light beam whose incident angle is 0 degrees is 680 nm. In addition, the dashed line indicates the spectrum of excitation light α whose main wavelength is 635 nm, and the chain double-dashed line indicates the spectrum of fluorescence γ whose main wavelength is 670 nm. Here, the "excitation light" includes not only excitation light α but also light (plasmon scattering light β) having a wavelength identical to that of excitation light α.

As illustrated in FIG. 5A, the cut off wavelength (640 nm) of wavelength separation filter 144 is set to a value between the main wavelength (635 nm) of excitation light α whose incident angle is a peak incident angle (35 degrees) and the main wavelength (670 nm) of fluorescence γ whose incident angle is a peak incident angle (35 degrees). That is, the light transmittance of wavelength separation filter 144 for the light beam of the main wavelength (670 nm) of fluorescence γ whose incident angle is a peak incident angle (35 degrees) is greater than the light transmittance of wavelength separation filter 144 for the light beam of the main wavelength (635 nm) of excitation light α whose incident angle is a peak incident angle (35 degrees). With this configuration, wavelength separation filter 144 selectively allows the light beam of fluorescence γ whose incident angle is the peak incident angle (35 degrees) to pass therethrough, and blocks most of the light beam of excitation light α whose incident angle is the peak incident angle (35 degrees). Accordingly, since the incident angle of the light beam to wavelength separation filter 144 and the incident angle of the light beam to light reception surface 146 of light sensor 145 are equal to each other as described above, wavelength separation filter 144 can selectively allow for transmission of most of fluorescence γ which is incident on light reception surface 146 of light sensor 145 at a peak incident angle (35 degrees).

On the other hand, as illustrated in FIG. 5B, the cut off wavelength (680 nm) of wavelength separation filter 144 for a light beam whose incident angle is 0 degrees is shifted to the long wavelength side in comparison with the case of a light beam whose incident angle is peak incident angle (35 degrees). In wavelength separation filter 144 (long pass filter) used in the present embodiment, the cut off wavelength is shifted to the long wavelength side by approximately 40 nm. As a result, wavelength separation filter 144 can more surely block excitation light α. In the case where the difference between the main wavelength of excitation light α and the main wavelength of fluorescence γ is small, wavelength separation filter 144 may possibly block not only excitation light α but also a part of fluorescence γ. However, by more surely blocking excitation light α, improvement in S/N ratio can be achieved.

As described, the wavelength separation property of wavelength separation filter 144 used in the present embodiment has angle dependence, and is optimized for a light beam whose incident angle is a peak incident angle (35 degrees). That is, the light transmittance of wavelength separation filter 144 for a light beam of the main wavelength of fluorescence γ whose incident angle is a peak incident angle (hereinafter also referred to as "Tτ") is greater than the light transmittance of wavelength separation filter 144 for a light beam of the main wavelength of fluorescence γ whose incident angle is 0 degrees (hereinafter also referred to as "T0") (Tτ>T0). Accordingly, as described above, improvement in efficiency and the S/N ratio can be achieved.

In addition, from the viewpoint of further improving the S/N ratio, wavelength separation filter 144 in which the cut off wavelength is shifted to the long wavelength side with respect to the main wavelength of excitation light α may be used. The reason for this is that improvement of S/N ratio can be expected by more surely blocking excitation light α even when the transmittance of fluorescence γ is reduced. For example, T0/Tτ<1/5 is preferable.

(Simulation)

In SPFS device 100 according to the present embodiment, the relationship between the incident angle and the light quantity of fluorescence γ at light reception surface 146 of light sensor 145 was simulated. On the light path from detection object region 31 in channel 41 to light reception surface 146, channel closure 40, light guiding rod 141, wavelength separation filter 144 and light sensor 145 are disposed in this order from detection object region 31 side. In addition, the light emitted from emission surface 143 of light guiding rod 141 passes through wavelength separation filter 144 and thereafter reaches light reception surface 146 through the sensor window. The parameters for the simulation are as follows: the height of channel closure 40: 0.1 mm, the refractive index of channel closure 40 (PMMA): 1.49, maximum length D' of detection object region 31: 3.0 mm, the axial length of light guiding rod 141: 16.0 mm, diameter D of light guiding rod 141: 14.0 mm, refractive index n of light guiding rod 141: 1.514, the distance between detection object region 31 and incidence surface 142 of light guiding rod 141: 0.6 mm, the length (thickness) of the wavelength separation filter in the axis direction of light guiding rod 141: 1.0 mm, the refractive index of wavelength separation filter 144: 1.514, the length (thickness) of the sensor window in the axis direction of light guiding rod 141: 0.8 mm, the refractive index of the sensor window (borosilicate glass): 1.487, the distance between wavelength separation filter 144 and sensor window: 0.5 mm, and the maximum length of light reception surface 146: 8.0 mm.

Figure 6:
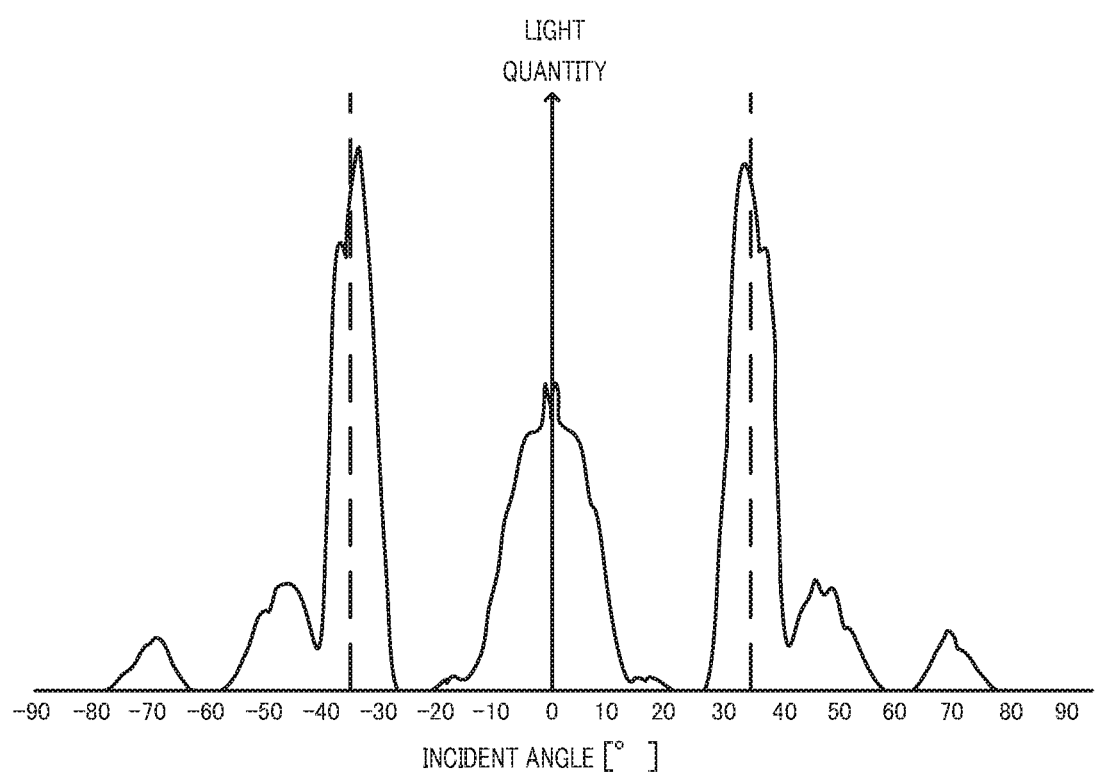
FIG. 6 illustrates a simulation of a relationship between the incident angle and the light quantity of fluorescence at the reception surface of the light sensor light.

FIG. 6 shows a simulation of the relationship between the incident angle and the light quantity of fluorescence γ at light reception surface 146 of light sensor 145. As illustrated in FIG. 6, it can be said that the light quantity of fluorescence γ emitted from detection object region 31 is maximized when it is incident on light reception surface 146 at an incident angle of around 35 degrees. Accordingly, in this case, wavelength separation filter 144 is selected such that light transmittance (Tτ) of wavelength separation filter 144 for a light beam of the main wavelength of fluorescence γ which is incident on light reception surface 146 at incident angle of 35 degrees (peak incident angle) is greater than the light transmittance of wavelength separation filter 144 for a light beam of the main wavelength of the excitation light which is incident on light reception surface 146 at an incident angle of 35 degrees, and greater than light transmittance (T0) of wavelength separation filter 144 for a light beam of the main wavelength of fluorescence γ which is incident on light reception surface 146 at an incident angle of 0 degrees. To be more specific, wavelength separation filter 144 is selected such that the light transmittance of wavelength separation filter 144 for a light beam of the main wavelength of fluorescence γ which is incident on wavelength separation filter 144 at an incident angle of 35 degrees is greater than the light transmittance of wavelength separation filter 144 for a light beam of the main wavelength of the excitation light which is incident on wavelength separation filter 144 at an incident angle of 35 degrees, and greater than the light transmittance of wavelength separation filter 144 for a light beam of the main wavelength of fluorescence γ which is incident on wavelength separation filter 144 at an incident angle of 0 degrees. With this configuration, wavelength separation filter 144 can block a light beam of excitation light α which is incident on light reception surface 146 at the peak incident angle, and can selectively allow for transmission of a light beam of fluorescence γ which is incident on light reception surface 146 at the peak incident angle. While wavelength separation filter 144 may possibly block a part of a light beam of fluorescence γ which is incident on light reception surface 146 at an incident angle of 0 degrees, wavelength separation filter 144 can more surely block a part of a light beam of excitation light α which is incident on light reception surface 146 at an incident angle of 0 degrees. As a result, SPFS device 100 according to the present embodiment can efficiently detect fluorescence γ with a high S/N ratio.

(SPFS Device Operation)

Figure 7:
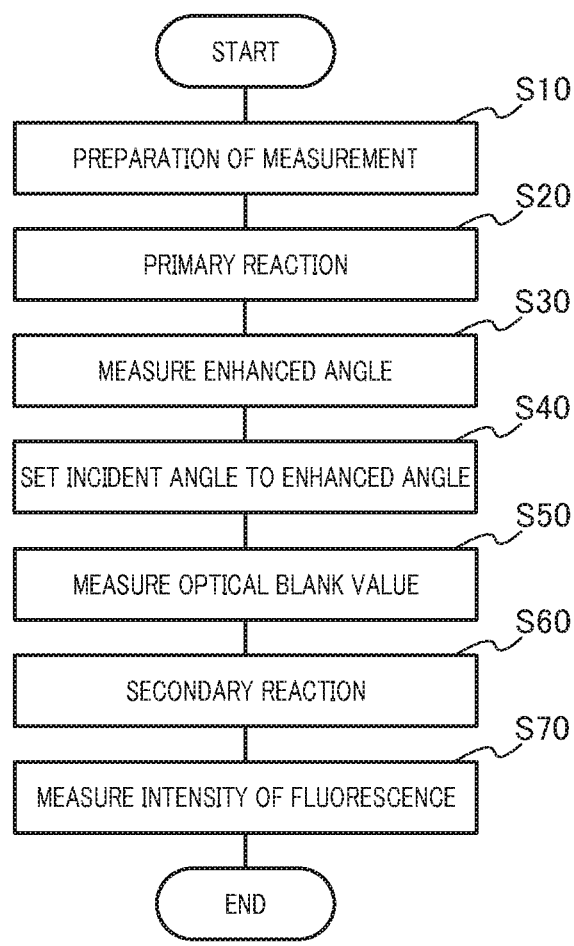
FIG. 7 is a flowchart of an exemplary operation procedure of the surface plasmon enhanced fluorescence measurement device.

Next, an operation of SPFS device 100 (a detection method using SPFS device 100) is described. FIG. 7 is a flowchart of an exemplary operation procedure of the SPFS device.

First, preparation for measurement is performed (step S10). To be more specific, detection chip 10 including detection object region 31 in which the capturing body for capturing the detection object substance is fixed is installed at a predetermined position of SPFS device 100. When a conserved reagent presents in channel 41 of detection chip 10, the inside of channel 41 is washed to remove the conserved reagent so that the capturing body can appropriately capture the detection object substance.

Next, a reaction between the detection object substance in the sample and the capturing body is caused (primary reaction, step S20). To be more specific, the sample is injected into channel 41, and the sample and the capturing body are brought into contact with each other. When the detection object substance is present in the sample, at least a part of the detection object substance is captured by the capturing body. Thereafter, the inside of channel 41 is washed with buffer solution or the like to remove materials which have not been captured by the capturing body. The kind of the sample is not limited. Examples of the sample include bodily fluids such as blood, serum, plasma, urine, nasal mucus, saliva, and semen, and their diluted solutions.

Next, while irradiating a predetermined area of metal film 30 (film formation surface 22) with excitation light α, the incident angle of excitation light α with respect to metal film 30 (film formation surface 22) is scanned, and an optimum incident angle is determined (step S30). To be more specific, control processing section 163 controls light source unit 121 and angle adjusting section 122 to scan the incident angle of excitation light α with respect to metal film 30 (film formation surface 22) while irradiating a predetermined area of metal film 30 (film formation surface 22) with excitation light α. In addition, control processing section 163 controls filter control section 164 to move wavelength separation filter 144 to a position outside the light path of light reception optical system 140 such that light sensor 145 detects plasmon scattering light β from detection object region 31, and control processing section 163 controls light sensor control section 162 to detect plasmon scattering light β. Plasmon scattering light β from detection object region 31 reaches light sensor 145 through light guiding rod 141. In this manner, control processing section 163 obtains data containing a relationship between the incident angle of excitation light α and the intensity of plasmon scattering light β. Then, control processing section 163 analyzes the data and determines the incident angle (enhanced angle) at which the intensity of plasmon scattering light β is maximized. While the enhanced angle is basically determined based on the material and the shape of prism 20, the thickness of metal film 30, the refractive index of the liquid in channel 41 and the like, the enhanced angle is also slightly varied by various factors such as the kind and the amount of the fluorescence material in channel 41, and shaping errors of prism 20. In view of this, it is preferable to determine the enhanced angle each time analysis is performed. The enhanced angle is determined in the order of about 0.1 degree.

Next, the incident angle of excitation light α with respect to metal film 30 (film formation surface 22) is set to the enhanced angle determined at the preceding step (step S40). To be more specific, control processing section 163 controls angle adjusting section 122 to set the incident angle of excitation light α with respect to metal film 30 (film formation surface 22) to the enhanced angle. In the following steps, the incident angle of excitation light α with respect to metal film 30 (film formation surface 22) is kept at the enhanced angle.

Next, metal film 30 (film formation surface 22) is irradiated with excitation light α, and the intensity of light having a wavelength same as that of fluorescence γ (optical blank value) is measured (step S50). To be more specific, control processing section 163 controls filter control section 164 that controls the filter movement section to move wavelength separation filter 144 to a position on the light path of light reception optical system 140. Subsequently, control processing section 163 controls light source control section 161 to emit excitation light α to light source unit 121. Simultaneously, control processing section 163 controls light sensor control section 162 such that light sensor 145 detects the intensity of light having a wavelength same as that of fluorescence γ. Thus, light sensor 145 can correctly measure the intensity of light (optical blank value) which results in noise. The measurement value is sent to control processing section 163 and recorded as an optical blank value.

Next, the detection object substance that has been captured by the capturing body is labeled by a fluorescence material (secondary reaction, step S60). To be more specific, a fluorescence labeling solution is injected into channel 41. The fluorescence labeling solution is, for example, a buffer solution containing an antibody (secondary antibody) labeled by a fluorescence material. When the fluorescence labeling solution is injected into channel 41, the fluorescence labeling solution makes contact with the detection object substance, and the detection object substance is labeled by the fluorescence material. Thereafter, the inside of channel 41 is washed with buffer solution and the like to remove the free fluorescence material and the like.

Finally, metal film 30 (film formation surface 22) is irradiated with excitation light α, and the intensity of fluorescence γ (weak light) emitted from detection object region 31 (label material) and guided by light guiding rod 141 is measured with light sensor 145 (step S70). To be more specific, control processing section 163 controls light source control section 161 such that light source unit 121 emits excitation light α. Simultaneously, control processing section 163 controls light sensor control section 162 such that light sensor 145 detects fluorescence γ emitted from detection object region 31. Control processing section 163 subtracts the optical blank value from the measurement value to calculate a fluorescence intensity correlated with the amount of the detection object substance. The fluorescence intensity is converted to the amount or the concentration of the detection object substance and the like as necessary.

As described above, in SPFS device 100 according to the present embodiment, $0.8n2D<L<1.2n2D$ is satisfied where D represents the diameter of incidence surface 142 of light guiding rod 141, L represents the axial length of light guiding rod 141 having a columnar shape, and n2 represents the refractive index of light guiding rod 141. With this configuration, most of fluorescence γ emitted from the fluorescence material is condensed in a region around a position remote from incidence surface 142 of light guiding rod 141 by diameter D of light guiding rod 141, and reaches light reception surface 146 of light sensor 145. At this time, the light quantity of fluorescence γ which reaches light reception surface 146 is maximized at a predetermined angle other than 0 degrees (peak incident angle). Accordingly, by optimizing the wavelength separation property of wavelength separation filter 144 for light which is incident on light reception surface 146 at the peak incident angle, SPFS device 100 can efficiently detect fluorescence γ with a high S/N ratio, while preventing upsizing.

It is to be noted that wavelength separation filter 144 may be integrated with light guiding rod 141. For example, light guiding rod 141 and wavelength separation filter 144 may be integrated by forming a dielectric multi-layer film on incidence surface 142 or emission surface 143 of light guiding rod 141. With this configuration, SPFS device 100 can be downsized and simplified.

Figure 8A:
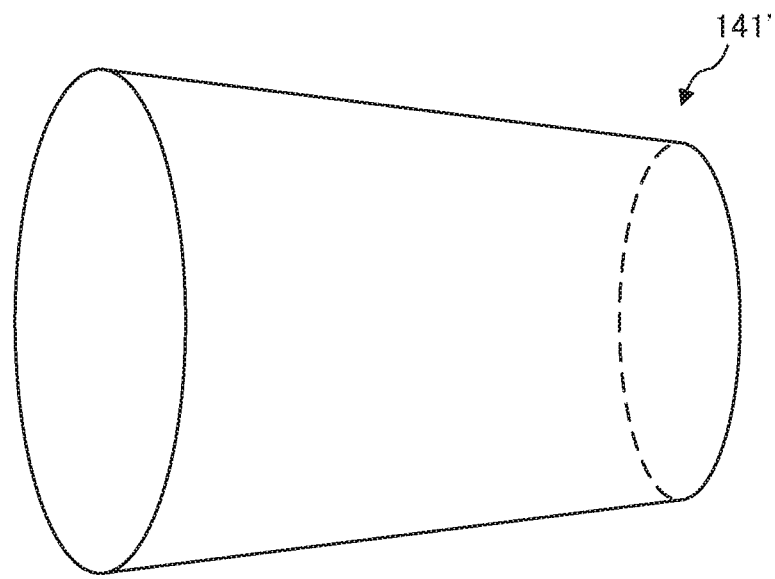
FIG. 8A is a perspective view of a light guiding rod according to a modification of the embodiment of the present invention.
Figure 8B:
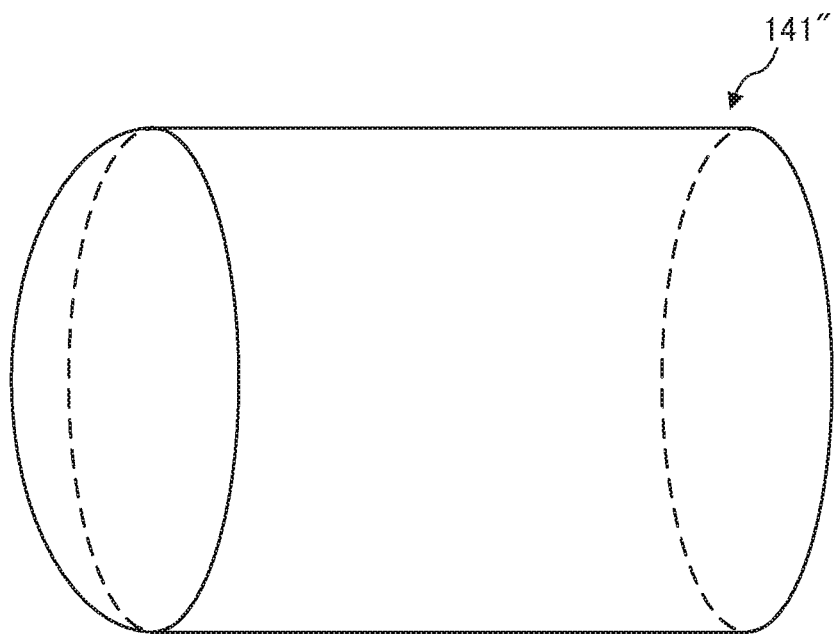
FIG. 8B is a perspective view of a light guiding rod according to a modification of the embodiment of the present invention.

While SPFS device 100 including light guiding rod 141 having a columnar shape is described in the present embodiment, the shape of light guiding rod 141 is not limited to the columnar shape. FIGS. 8A and 8B are perspective views of light guiding rods 141' and 141'' according to a modification of the embodiment of the present invention. For example, as illustrated in FIG. 8A, the light guiding rod may be tapered light guiding rod 141' whose cross-sectional area gradually decreases from the incidence surface toward the emission surface, or tapered light guiding rod 141' whose cross-sectional area gradually increases from the incidence surface toward the emission surface.

With tapered light guiding rod 141' whose cross-sectional area gradually decreases from the incidence surface toward the emission surface, a large quantity of light can be taken in at the wide incidence surface, and emitted toward light sensor 145 while being condensed at the narrow emission surface. As a result, in the SPFS device having tapered light guiding rod 141' whose cross-sectional area gradually decreases from the incidence surface toward the emission surface, light sensor 145 in which light reception surface 146 has a small area can be adopted. From the standpoint of cost reduction and downsizing of the detection device, it is preferable to adopt light sensor 145 in which light reception surface 146 has a small area. In addition, in general, the greater the area of the light reception surface of light sensor 145, the greater the amount of noise. Therefore, in a detection device for detecting weak light, it is preferable to adopt light sensor 145 in which light reception surface 146 has a small area also from the standpoint of detecting fluorescence γ with a high S/N ratio.

On the other hand, in tapered light guiding rod 141' whose cross-sectional area gradually increases from the incidence surface toward the emission surface, light incident on the incidence surface is reflected by the tapered surface in light guiding rod 141'. With this configuration, the emission angle of a light beam emitted from the emission surface with respect to the emission surface can be a set to a small angle in comparison with the incident angle of a light beam incident on the incidence surface with respect to the incidence surface. As a result, in comparison with the case where light guiding rod 141 having a columnar shape is used, the peak incident angle can be set to a smaller angle. In the above-described embodiment, wavelength separation filter 144 optimized for a light beam whose incident angle is the peak incident angle (35 degrees) is used. It is assumed that the peak incident angle is changed from 35 degrees to 30 degrees. When the incident angle to wavelength separation filter 144 is changed from 35 degrees to 0 degrees, the cut off wavelength is changed from 640 nm to 680 nm, that is, the cut off wavelength is shifted to the long wavelength side by 40 nm (see FIGS. 5A and 5B). In contrast, when wavelength separation filter 144 optimized for a light beam whose incident angle is the peak incident angle (30 degrees) is used, the cut off wavelength is shifted to the long wavelength side by only about 30 nm. That is, when it is assumed that FIGS. 5A and 5B show the wavelength separation property of the wavelength separation filter optimized for a light beam whose incident angle is 30 degrees, the cut off wavelength of the wavelength separation filter for a light beam whose incident angle is 0 degrees is 670 nm in FIG. 5B when the cut off wavelength of the wavelength separation filter for a light beam of whose incident angle is 30 degrees is 640 nm in FIG. 5A. As a result, when tapered light guiding rod 141' whose cross-sectional area gradually increases from the incidence surface toward the emission surface is used, wavelength separation filter 144 can surely block excitation light α. Moreover, while a part of fluorescence γ is blocked since the cut off wavelength for an incident angle of 0 degrees is 670 nm, the light quantity of fluorescence γ to be blocked can be reduced in comparison with the case where the cut off wavelength is 680 nm (in the case of peak incident angle of 35 degrees). That is, the SPFS device can increase the light quantity of fluorescence γ to be detected, and can further improve the S/N ratio while surely blocking excitation light α.

In addition, light guiding rod 141" whose incidence surface or emission surface has a shape of a convex lens as illustrated in FIG. 8B may also be adopted. Further, although not illustrated in the drawings, a light guiding rod whose incidence surface and emission surface have a shape of a convex lens may also be adopted. With such configurations, fluorescence γ emitted from detection object region 31 can be efficiently condensed at light reception surface 146 of light sensor 145. Accordingly, fluorescence γ can be efficiently detected with a high S/N ratio.

While the measurement of the enhanced angle (step S30) is performed after the primary reaction (step S20) in the above-described embodiment, the order of the steps in the detection device according to the present invention is not limited to this. For example, measurement of the enhanced angle may be performed before the primary reaction. With this configuration, it is possible to prevent the enhanced angle from being changed by the materials non-specifically adsorbed in the channel of the detection chip due to the primary reaction. In addition, in the case where the incident angle of excitation light α is determined in advance, the measurement of the enhanced angle may be omitted.

This application is entitled to and claims the benefit of Japanese Patent Application No. 2014-126282 filed on Jun. 19, 2014, the disclosure each of which including the specification, drawings and abstract is incorporated herein by reference in its entirety.

INDUSTRIAL APPLICABILITY

The detection device according to the present invention can efficiently detect weak fluorescence emitted from a label material with a high S/N ratio, and is suitable for laboratory tests and the like for example.

REFERENCE SIGNS LIST

10 Detection chip
20 Prism
21 Incidence surface of prism
22 Film formation surface of prism
23 Emission surface of prism
30 Metal film
31 Detection object region
40 Channel closure
41 Channel
100 Surface plasmon resonance fluorescence analysis device (SPFS device)
110 Chip holder
120 Excitation optical system unit
121 Light source unit
122 Angle adjusting section
140 Light reception optical system
141, 141', 141" Light guiding rod
142 Incidence surface of light guiding rod
143 Emission surface of light guiding rod
144 Wavelength separation filter
145 Light sensor
146 Light reception surface
160 Control section
161 Light source control section
162 Light sensor control section
163 Control processing section
164 Filter control section θ1 Incident angle of light beam incident on light guiding rod
θ2 Refraction angle of light beam incident on light guiding rod
n1, n2 Refractive index
D Diameter of light guiding rod
D' Maximum length of detection object region
D" Maximum length of light reception surface of light sensor
L Axial length of light guiding rod
α Excitation light
β Plasmon scattering light
γ Fluorescence

What is claimed is:

1. A detection device comprising:
   a light source that irradiates a detection object substance labeled by a fluorescence material with excitation light;
   a light sensor that detects fluorescence generated by irradiating the detection object substance with the excitation light;
   a light guiding rod that guides the fluorescence to the light sensor; and
   a wavelength separation filter disposed at a position between the detection object substance and the light sensor,
   wherein a light transmittance of the wavelength separation filter for a light beam of a main wavelength of the fluorescence which is incident on a light reception surface of the light sensor at a predetermined peak incident angle is higher than a light transmittance of the wavelength separation filter for a light beam of a main wavelength of the excitation light which is incident on the light reception surface at the predetermined peak incident angle;
   wherein the predetermined peak angle is an angle higher than 0 degrees.

2. The detection device of claim 1,
   wherein the light transmittance of the wavelength separation filter for a light beam of a main wavelength of the fluorescence which is incident on the light reception surface of the light sensor at the predetermined peak incident angle is higher than a light transmittance of the wavelength separation filter for a light beam of a main wavelength of the fluorescence which is incident on the light reception surface of the light sensor at an incident angle of 0 degrees.

3. The detection device of claim 2,
   wherein the light transmittance of the wavelength separation filter for the light beam of the main wavelength of the fluorescence which is incident on the light reception surface at the incident angle of 0 degrees is not higher than one-fifth of the light transmittance of the wavelength separation filter for the light beam of the main wavelength of the fluorescence which is incident on the light reception surface at the predetermined peak incident angle.

4. The detection device of claim 1,
   wherein in a relationship between a light quantity and an incident angle of the fluorescence at the light sensor, the peak incident angle which is an incident angle at which the light quantity of the fluorescence is maximized.

5. The detection device of claim 1,
   wherein the predetermined peak incident angle is greater than 0 degrees and less than 45 degrees.

6. The detection device of claim 1,
   wherein the predetermined peak incident angle is between 30 degrees and 35 degrees.

7. The detection device of claim 1,
   wherein the wavelength separation filter is integrated with the light guiding rod.

8. The detection device of claim 1,
   wherein the light reception surface is perpendicular to an axis direction of the light guiding rod, and
   wherein the wavelength separation filter is disposed along a direction perpendicular to the axis direction of the light guiding rod.

9. The detection device of claim 1,
   wherein the light guiding rod has a columnar shape.

10. The detection device of claim 1, further comprising a detection chip that includes a prism, and a metal film disposed on the prism, wherein:
    the detection object region is at least a part of a surface of the metal film;
    the light source applies, from the prism side, excitation light to a rear surface of the metal film;
    the fluorescence is a fluorescence which is emitted from the fluorescence material which is excited by localized light generated by the excitation light applied to the rear surface of the metal film through the prism.

* * * * *